United States Patent [19]
Anderson et al.

[11] Patent Number: 5,690,246
[45] Date of Patent: Nov. 25, 1997

[54] SECURITY CONTAINERS FOR SAMPLES

[75] Inventors: Ian Denny Anderson; Michael Denny Anderson, both of Kent, Great Britain

[73] Assignee: Versapak (International) Ltd., Erith, Great Britain

[21] Appl. No.: 659,620

[22] Filed: Jun. 6, 1996

Related U.S. Application Data

[63] Continuation of Ser. No. 381,933, Feb. 13, 1995, abandoned.

[30] Foreign Application Priority Data

Aug. 11, 1992 [GB] United Kingdom ............. 9216955

[51] Int. Cl.[6] ............................................. B65D 47/08
[52] U.S. Cl. ................ 220/254; 220/789; 220/790; 206/807; 206/446
[58] Field of Search .................... 220/254, 789, 220/790, 339; 206/807, 446

[56] References Cited

U.S. PATENT DOCUMENTS

| | | |
|---|---|---|
| 4,452,382 | 6/1984 | Von Holdt . |
| 4,534,467 | 8/1985 | Rathbun . |
| 4,693,399 | 9/1987 | Hickman et al. ............... 220/254 |
| 4,873,193 | 10/1989 | Jensen et al. . |
| 4,936,494 | 6/1990 | Weidman ...................... 220/254 |
| 5,273,177 | 12/1993 | Campbell ...................... 220/254 |

FOREIGN PATENT DOCUMENTS 9207770  5/1992  European Pat. Off. .

Primary Examiner—Joseph M. Moy
Attorney, Agent, or Firm—Dowell & Dowell

[57] ABSTRACT

The invention provides a container for a sample comprising a hollow body having a base, a side wall and an open end opposite the base, a closure for that body, the closure being arranged to fit to the body to close the open end thereof; and locking means for locking the closure to the body, in such fashion that the contents of the container cannot be removed without it being apparent on subsequent observation of the container. Preferably said closure is provided with a tear-off portion defined thereon by a line of weakness in the material of the closure, removal of the tear-off portion by tearing along said line of weakness allowing removal of the sample from the body.

16 Claims, 2 Drawing Sheets

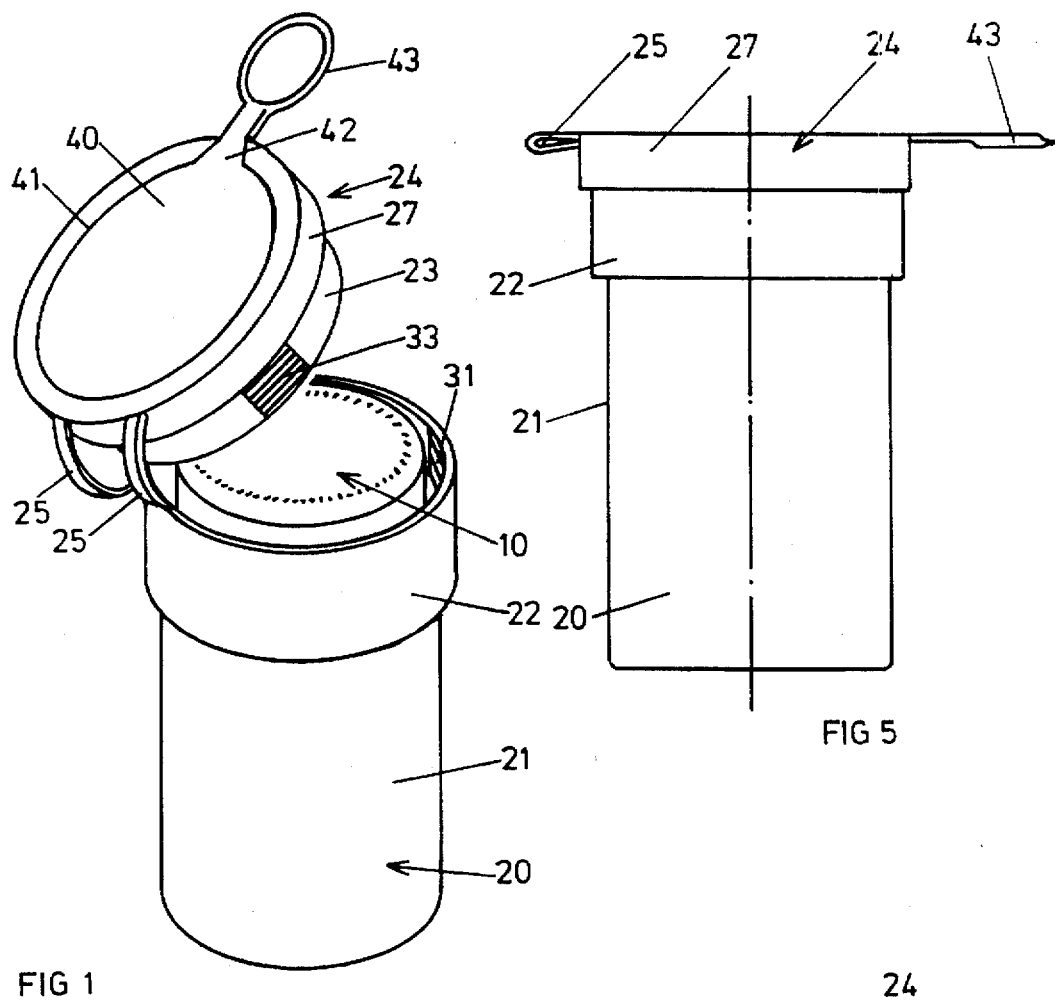
FIG 1
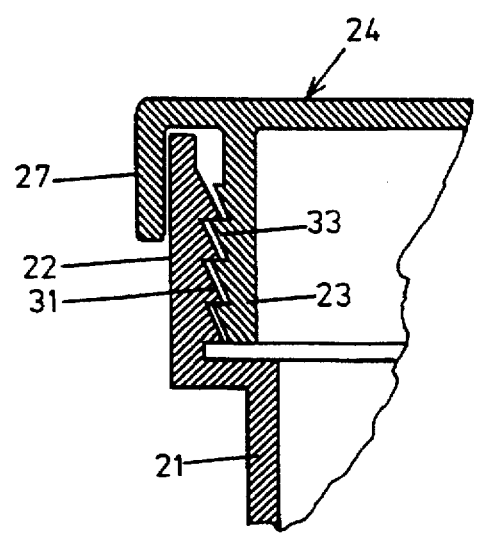
FIG 5
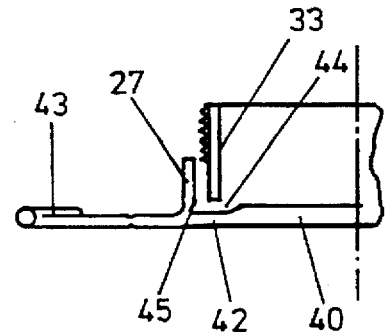
FIG 7
FIG 6

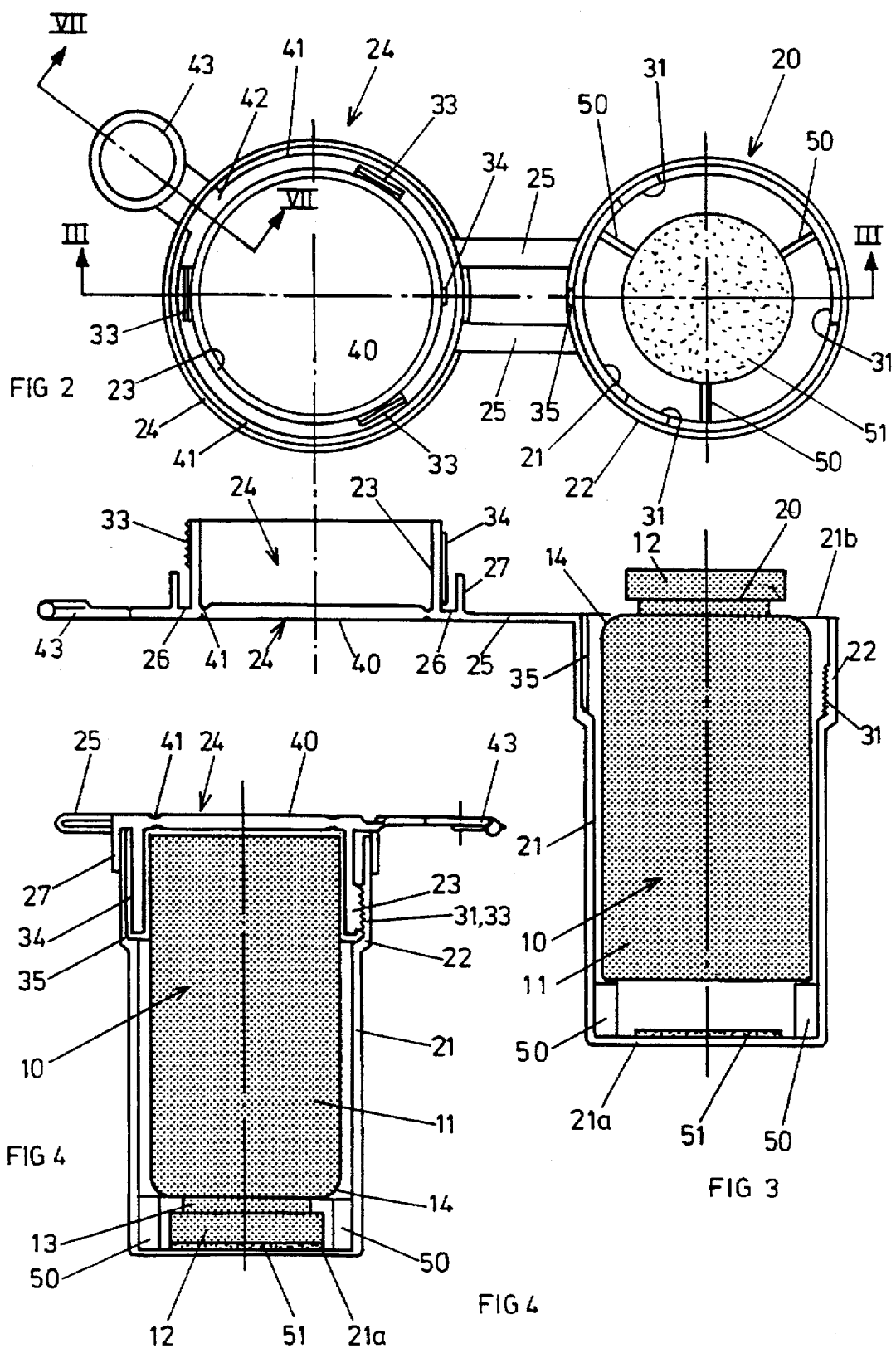

SECURITY CONTAINERS FOR SAMPLES

This application is a continuation of application Ser. No. 08/381,933, filed Feb. 13, 1995 now abandoned.

BACKGROUND OF THE INVENTION

1. Field of the Invention

This invention relates to a container suitable for holding a sample of liquid or solid material in a secure and tamperproof manner.

The invention finds particular, but not exclusive, application in the provision of a sample container for biological samples such as urine samples taken in drug testing procedures for athletes.

The sample taken for such purposes is normally stored in a standard glass bottle or jar, having a normal sealed screw cap which is readily releasable. There is a requirement to secure such a sample bottle in a tamper-proof fashion so that it is not possible to interfere with the contents once the bottle has been closed and sealed. It is also desirable to provide a container for the transport of such sample bottles which will afford a measure of protection to the bottle against breakage in transit.

SUMMARY OF THE INVENTION

It is therefore an object of the present invention to provide a container for such bottles or other items which can be closed with the sample bottle inside, in a tamper-proof fashion, so that it is readily apparent if there has been any interference of the contents.

It should be understood however, that the invention has wider application, and may be used to store other samples of material, liquid or sold, with or without the use of a sample bottle.

Accordingly, in its broadest aspect, the present invention provides a container for a sample comprising a hollow body and a closure for that body, the closure being arranged to fit to the body to close and seal it in such fashion that the contents of the container cannot be removed without it being apparent on subsequent observation of the container.

Preferably the closure is provided with locking means which cooperates with the body to allow the closure to be freely positioned on the body to close the body, but which prevents removal of the closure from the body without damage to either the closure or the body.

Preferably the closure is formed with a tear-out portion defined from the remainder of the closure by a line of weakness, which tear-out portion may be removed to allow the authorised removal of the contents of the container.

Preferably the container is arranged to contain a sample bottle or jar which preferably has its own releasable closure to seal any contents therein.

BRIEF DESCRIPTION OF THE DRAWINGS

In order to promote a fuller understanding of the above and other aspects of the present invention, an embodiment will now be described, by way of example only, with reference to the accompanying drawings in which FIG. 1 shows a perspective view of a sample container embodying the invention, with a sample bottle therein, ready to be sealed in the container, FIG. 2 is a plan view of the container of FIG. 1, without the sample bottle and with the closure of the container folded back, FIG. 3 is a cross-section on the line III—III of FIG. 2 with a sample bottle shown in the container before use, FIG. 4 is a similar cross-section to that of FIG. 3, only with the sample bottle retained in the container with the closure in a sealed position on the container, FIG. 5 is an external side view similar to that of FIG. 4, FIG. 6 is a schematic cross-section (not to scale) showing in detail the locking means between the closure and the container of the previous figures, and FIG. 7 is a schematic cross-section (not to scale) on the line VII—VII of FIG. 2.

DESCRIPTION OF THE PREFERRED EMBODIMENT

The embodiment of the invention shown in the drawings is arranged for use with a sample bottle which may contain a liquid or solid sample.

A typical sample bottle is shown in the drawings at 10 having a body 11 and a removable screw or bayonet fitting fluid tight cap 12 or a necked portion 13 separated from the body 11 by a shoulder 14, all of which are of conventional design per se, A container for the bottle 10, which embodies the invention, is shown in schematic perspective view at FIG. 1. The container comprises a main hollow body portion 20 having a base 21a, a side wall 21, and an open end 21b opposite the base portion 21a, and which is shaped to receive the sample bottle 10, and which has an enlarged upper portion 22. A closure for the container, which is in the form of a cover which is indicated generally at 24, and includes a skirt portion 23 which, in the closed or sealed position, seats in the enlarged upper portion 22 of the container body.

The cover 24 is flexibly attached to the body 20 of the container by means of two bridging pieces 25; and is arranged so that as the bridging pieces 25 are folded over, from the situation shown in FIGS. 2 and 3, through that as shown in FIG. 1, to the situation shown in FIGS. 4 and 5, the skirt 23 may be inserted in the enlarged portion 22 of the container body to position the cover on the container. The cover 24 has a flange 26 arranged to overlie the top edge 21c of the enlarged portion 22, and a further, outer, skirt 27 which extends down over the outer surface of the upper part of the enlarged portion 22 when the cover is in the closed position, as seen particularly in FIGS. 4 and 5.

In order to secure the cover in the closed position, a number of locking means, in this embodiment three, are provided to be operative between the body portion 20 and the cover 24, and spaced around the peripheries thereof. The locking means, of this embodiment, each comprise a first series of ratchet teeth 31 formed locally on the inner surface of the enlarged portion 22 of the body of the container; and a second series of ratchet teeth 33 formed locally on a corresponding position on the outer surface of the skirt 23 of the cover 24. The first and second ratchet teeth are arranged so that the cover 24 can be pushed into place from the position shown in FIG. 1 to that shown in FIG. 4 with the teeth riding over one another. However, once the cover is in position, the ratchet teeth lock it against removal so that the container is securely sealed.

The skirt portion 23 of the cover 24, is formed with a key 34 which is arranged to cooperate with a keyway 35 formed in the inner surface of the enlarged portion 22 of the body 20, when the cover is positioned on the body. Thus the cover is angularly located relative to the body to ensure that the first and second sets of ratchet teeth are correctly aligned when the cover is placed in position.

In order to permit authorised removal of the bottle 10 from a closed and sealed container, the central portion 40 of the cover 24 is defined from the remainder of the cover structure by a line of weakness indicated at 41, which is generally circular but extends outwards to the periphery of the cover to form a tab 42. The tab 42 is extended to form a loop-like handle 43 which a user may grip to tear the central or tear-off portion 40 from the remainder of the cover 24 along the line of weakness 41, As best seen in FIG. 7, the skirt portion 23 is formed with a local aperture 44, and the outer skirt portion 27 is locally weakened as shown at 45, to enable the central portion to be so torn away at the periphery of the cover.

Removal of the central portion 40 in this manner, provides an aperture in the top of the closed container through which the bottle 10 may be removed. However it is to be noted that since the material of the cover is torn for such removal, this cannot be achieved without it being immediately apparent that the container has been opened. The line of weakness 41 can be formed by suitable grooves as indicated at 46 in FIG. 6. As shown in the drawings, the tear-off portion is generally flat and coplanar with the flange 26 of the closure.

The conventional bottle used with this embodiment of the invention is necked and has a screw top 12 which is generally slightly smaller than the overall body 11 of the bottle. The bottom of the container body 20 is provided with ribs 50 which are so arranged as to support the bottom of the body 11 of the bottle 10, with the screw cap 12 proud of the top of the container, as shown in FIG. 3, when the bottle is placed in the container with its screw cap upwards. In this situation, the screw cap 12 extends sufficiently far out of the container to prevent the cover 24 being pushed into position to engage the locking means 30. Thus the container cannot then be accidentally closed before its intended use.

When it is desired to seal a bottle 10 in the container, it is placed in the body 20 of the container, screw cap downwards as shown in FIG. 4, the ribs 50 being arranged to accommodate the screw cap 12 between them, and in this situation the bottom of the bottle does not extend above the body of the container and the cover 24 can be pushed fully home to seal the container, as shown in FIG. 4. A resilient material pad 51 is provided in the bottom of the body 20 of the container to prevent the bottle rattling in the closed container.

In a modification of the embodiment shown in the drawings, the handle 43 may include a suitable aperture by means of which it may be secured, when the cover is in its closed position, to the outer face of the skirt 22, by means of a sealing button of known type per se sold under the Trade Mark "Versapak". This may provide an additional seal for the container, and thus additional security.

The container and cover are preferably molded, integrally in one piece, from synthetic plastic material of a suitable grade to provide an economic yet tough protective container for the bottle. The container may be marked with appropriate serial numbers or codes molded into the outer surface, particularly on the central portion 40 of the cover, so that the container, and the sample sealed therein may be uniquely identified. The body of the container may also be marked similarly, with the corresponding serial number or code.

The side wall 21 of the body 20 of the container, may be provided with a window (not shown in the drawings) along all or part of its height, so that the contents, either in a bottle within the container or within the container itself, may be obeserved without opening or otherwise tampering with the container.

Thus is can be seen that the invention provides a container which can seal a sample bottle in a tamper-proof fashion, and which provides for the safe transport of the sample bottle.

While the above embodiment has been discribed with the use of a sample bottle, it is to be understood that the container may also be used without a bottle to contain a sample, in which case the flange 26 of the closure (24) may be arranged to seal in fluid tight manner on the body (20). In cases where the sample is solid, such sealing would not be needed unless the sample was of a fine powder or similar material.

We claim:

1. A combination security container and sample bottle, comprising: a sample bottle, a container being adapted to receive the sample bottle therein, said container including a hollow body having a base, a side wall and an open end opposite said base, said open end defined by a top edge of said hollow body, a closure for said hollow body, said closure being arranged to fit said body to overlie said top edge of said hollow body and close the open end thereof, said closure forming a top for the container when said closure is fitted to overlie and close the open end of said hollow body with said sample bottle therein, and locking means for locking said closure to said hollow body, said closure including a tear-off portion defined by a line of weakness in said closure which is formed to permit the removal of said tear-off portion from the closure, said line of weakness defining an aperture through said closure of a size to permit the removal of said sample bottle therethrough only upon the effective removal of said tear-off portion from said closure along said line of weakness such that removal of said sample bottle from said container when said closure is fitted to close the opening in said hollow body without damage to said closure or said hollow body is possible only by the effective removal of said tear-off portion from said closure along said line of weakness, and the effective removal of said tear-off portion thereby being apparent on subsequent observation of said container.

2. A combination as claimed in claim 1, in which said tear-off portion comprises a substantial portion of said top of the container.

3. A combination as claimed in claim 2, in which said tear-off portion is provided with a handle by which it may be gripped to so tear said tear-off portion from said closure.

4. A combination as claimed in claim 3, in which said tear-off portion is formed by said line of weakness to have a tab which extends to a periphery of said closure and said handle is formed on said tab.

5. A combination as claimed in claim 1, in which said hollow body has an enlarged portion adjacent the open end and said closure is formed with a skirt portion arranged to fit into said enlarged portion when said closure is fitted to said hollow body.

6. A combination as claimed in claim 5, in which said closure is formed with a further skirt portion which is arranged to engage the outer surface of said enlarged portion when said closure is fitted to said hollow body.

7. A combination as claimed in claim 1, in which said locking means comprises a first series of ratchet teeth formed on said hollow body, and a second series of ratchet teeth formed on said closure, said first and second series of ratchet teeth being arranged to cooperate to allow free fitting of said closure on said hollow body and to prevent subsequent removal of said closure from said hollow body.

8. A combination as claimed in claim 7, in which said first and second series of ratchet teeth are formed over spaced peripheral portions of said closure and hollow body, respectively.

9. A combination as claimed in claim 1, in which said locking means comprises a first series of ratchet teeth formed on said hollow body, a second series of ratchet teeth formed on said closure, said first and second series of ratchet teeth being arranged to cooperate to allow free fitting of said closure on said hollow body and to prevent subsequent removal of said closure from said hollow body, said first series of ratchet teeth being formed on an inside surface of said enlarged portion and said second series of ratchet teeth being formed on an outside surface of said skirt portion.

10. A combination as claimed in claim 1, in which said closure and said hollow body are molded integrally as one piece, connected by at least one bridging member, from synthetic plastic material.

11. A combination as claimed in claim 1, in which said bottle is formed with an upper necked portion, a body portion having a base, and a shoulder connecting said necked portion to said body portion, said necked portion being of smaller size than said body portion, said hollow body being provide with bottle supports arranged to support said bottle by said base portion thereof with the necked portion extending through said open end of said hollow body of the container, thus to prevent fitting of said closure to said hollow body of the container; and said bottle supports being arranged to receive said necked portion of said bottle therebetween to support said bottle by said shoulder with said base portion of said bottle within said hollow body of the container, thus to allow the fitting of said closure to said hollow of the container.

12. A combination as claimed in claim 1, wherein said cover includes a flange extending outwardly from said tear-off portion, said flange and said tear-off portion being substantially coplanar.

13. The combination of claim 1 in which said closure includes a first depending generally annular skirt of a size to be seated inside of said top edge of said hollow body and a generally annular outer skirt of a size to extend outside of said top edge of said hollow body when said closure is fitted to overlie said hollow body, and said line of weakness having a generally circular portion oriented adjacent to and concentrically within said first annular skirt.

14. The combination of claim 13 in which said closure includes an outer peripheral edge adjacent said outer skirt, said line of weakness extending outwardly from said generally circular portion to said peripheral edge to define a tab formed integrally with said tear-off portion.

15. The combination of claim 14 wherein said first skirt includes an aperture underlying said tab of said tear-off portion and said outer skirt including a line of weakness proximate to said tab for facilitating effective removal of said tab and said tear-off portion from said closure.

16. The combination of claim 14 including a handle portion integrally formed with said tab and extending outwardly from said closure to facilitate in the effective removal of said tear-off portion from said closure.

* * * * *